United States Patent
Augelli-Szafran et al.

(10) Patent No.: US 6,812,228 B2
(45) Date of Patent: Nov. 2, 2004

(54) BENZOXAZINES FOR USE IN THE TREATMENT OF PARKINSON'S DISEASE

(75) Inventors: Corinne Elizabeth Augelli-Szafran, Ann Arbor, MI (US); Thomas Boehme, Ruesselsheim (DE); Roy Douville Schwarz, Howell, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/275,825

(22) PCT Filed: Apr. 17, 2001

(86) PCT No.: PCT/US01/12528

§ 371 (c)(1),
(2), (4) Date: Nov. 8, 2002

(87) PCT Pub. No.: WO01/85734

PCT Pub. Date: Nov. 15, 2001

(65) Prior Publication Data

US 2003/0220335 A1 Nov. 27, 2003

Related U.S. Application Data

(60) Provisional application No. 60/202,787, filed on May 9, 2000.

(51) Int. Cl.[7] ................ A61K 31/5365; C07D 498/14
(52) U.S. Cl. ...................... 514/229.5; 544/89
(58) Field of Search ............. 544/89; 514/229.5

(56) References Cited

PUBLICATIONS

Augelli–Szafran et al., "Identification and Characterization of m 4 Selective Muscarinic Antagonists", *Bioorg Med Chem Lett B*, 1998, pp. 1991–1996.

*Primary Examiner*—Richard L. Raymond
(74) *Attorney, Agent, or Firm*—Scully, Scott, Murphy & Presser

(57) ABSTRACT

Benzoxazines of Formula (I) wherein $R^1$ is $C_1$–$C_6$ alkyl, $C_2$–$C_6$ alkenyl, or $(CH_2)_n$ phenyl, $R^2$ is $C_3$–$C_6$ alkyl, $R^3$ is hydrogen, halo, hydroxy, alkoxy, or alkylthio, $R^4$ is hydrogen or alkyl, or a pharmaceutically acceptable salt thereof, are useful for treating movement disorders such as Parkinson's disease.

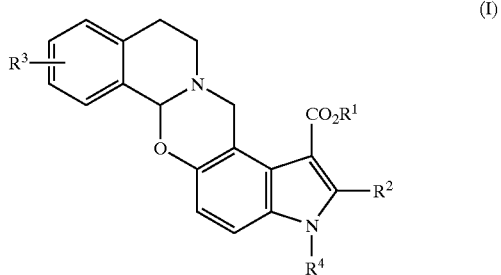

11 Claims, No Drawings

BENZOXAZINES FOR USE IN THE TREATMENT OF PARKINSON'S DISEASE

This application is a 371 application of PCT/US01/12528 filed Apr. 17, 2001, which claims the benefit of priority to United States provisional application Ser. No. 60/202,787 filed May 9, 2000.

FIELD OF THE INVENTION

This invention relates to treatment of movement disorders such as Parkinson's disease using certain benzoxazine compounds.

BACKGROUND OF THE INVENTION

Movement disorders are progressive neurodegenerative diseases characterized by hypokinesia, tremor, and muscular rigidity. One of the most common movement disorders is Parkinson's disease (PD). It results in a slowing of voluntary movements, a festinating gait, peculiar posture, and general weakness of muscles. There is progressive degeneration within the nuclear masses of the extrapyramidal system, and a characteristic loss of melanin-containing cells from the substantia nigra and a corresponding reduction in dopamine levels in the corpus striatum. The cause of PD is unknown, but it is widely believed that multifactorial genetic and environmental factors are contributors. While the disease can develop at any age, it is most common in adults, and typically afflicts people at about sixty years of age and older. Parkinson's disease is becoming a particularly serious disease given the aging population.

There are no known cures for movement disorders such as PD. The most common treatment has been the administration of levodopa, the precursor to dopamine, whose concentration in the substantia nigra is known to diminish as the disease progresses. Levodopa often produces unpleasant complications, resulting in even more serious health problems that are untreatable.

There are a group of monomeric proteins called muscarinic receptors found throughout the body of animals, including humans. These muscarinic receptors are present in the central nervous system, the peripheral nervous system, and in peripheral organs. There have now been five muscarinic receptor subtypes identified, and they are referred to as $M_1$, $M_2$, $M_3$, $M_4$, and $M_5$ receptors. These various receptors are present throughout the body, and the individual subtypes seem to be responsible for different actions. For example, in peripheral tissues, $M_1$ receptors amplify ganglionic neurotransmission. $M_2$ receptors cause reduced contractility and heart rate, while $M_3$ receptors cause contraction of smooth muscles. For muscarinic receptors in brain tissue, the $M_1$ receptors are responsible for memory and learning, the $M_2$ receptors are responsible for control of autonomic functions, and the $M_4$ receptors control motor behavior.

Compounds that antagonize muscarinic receptors have been developed for treatment of neurodegenerative diseases and movement disorders such as PD. Because the various muscarinic receptor subtypes are expressed in numerous body tissues, and each subtype appears to control or effect a different bodily function, it would be useful to find compounds that are selective for a single subtype. The $M_4$ subtype is found in high levels in the striatum of the brain and is responsible for motor function. Accordingly, compounds that selectively antagonize the $M_4$ receptor would be useful as treatments for movement disorders such as PD, without adversely affecting other body functions controlled by the other muscarinic receptor subtypes.

Augelli-Szafram et al., describe a series of benzoxazines that are said to be M4 selective muscarinic antagonists (*Bioorg. Med. Chem. Lett.* 8,1998;1991–1996). The compounds permit only hydrogen and methyl at the 2-position. We have now found a group of benzoxazine compounds having longer chain alkyl groups at the 2-position that are surprisingly potent and selective antagonists at the $M_4$ receptor. An object of this invention is to provide the compounds as new chemical entities, and a method for treating movement disorders utilizing such compounds.

SUMMARY OF THE INVENTION

This invention provides certain benzoxazine compounds, pharmaceutical compositions comprising them, and a method for treating movement disorders by administering them. More particularly, the invention is a benzoxazine of Formula I

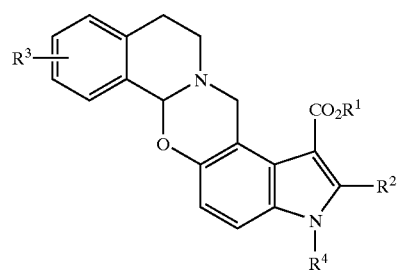

or a pharmaceutically acceptable salt thereof, wherein:

$R^1$ is $C_1$–$C_6$ allyl, $C_2$–$C_6$ alkenyl, or $(CH2)_n$ phenyl;
$R^2$ is $C_3$–$C_6$ alkyl;
$R^3$ is hydrogen, halo, hydroxy, O—$C_1$–$C_6$ alkyl, or S—$C_1$–$C_6$ alkyl;
$R^4$ is hydrogen, $C_1$–$C_6$ alkyl, or $(CH_2)_n$ phenyl; and
n is an integer from 0 to 3.

Preferred compounds have Formula I wherein $R^2$ is n-propyl.

Also preferred are compounds of Formula I wherein $R^1$ is ethyl.

The most preferred compounds have Formula I wherein $R^1$ is ethyl, $R^2$ is n-propyl, $R^4$ is hydrogen or methyl, and $R^3$ is $OCH_3$ or $SCH_3$.

Another embodiment of the invention is a pharmaceutical composition comprising a compound of Formula I together with a pharmaceutically acceptable diluent, excipient, or carrier therefor.

Another embodiment is a method for treating movement disorders such as Parkinson's disease comprising administering to a patient in need of treatment a compound of Formula I.

DETAILED DESCRIPTION OF THE INVENTION

As used herein, the term $C_1$–$C_6$ alkyl means straight and branched hydrocarbon chains having from 1 to 6 carbon atoms. Examples include methyl, ethyl, isopropyl, n-butyl, 1,1-dimethylbutyl, isohexyl, and neopentyl. "$C_3$–$C_6$ alkyl" means straight and branched hydrocarbon chains having from 3 to 6 carbon atoms, groups such as n-propyl, isopropyl, n-butyl, n-pentyl, isopentyl, and n-hexyl.

The term "O—$C_1$–$C_6$ alkyl" means the foregoing $C_1$–$C_6$ alkyl groups linked through an oxygen atom. Typical groups are methoxy, ethoxy, isopropoxy, tert-butoxy, n-pentyloxy, and n-hexyloxy. Similarly, "S—$C_1$–$C_6$ alkyl" means a $C_1$–$C_6$ alkyl group bonded through a sulfur atom. Examples include thiomethyl, thioethyl, thio-n-butyl, and thio-n-hexyl.

"$C_2$–$C_6$ alkenyl" means straight or branched alkyl groups having a double bond in the chain. Examples include ethenyl, 2-propenyl, 2-butenyl, 3-butenyl, 1-methyl-3-butenyl, and 3-hexanyl.

The group "$(CH_2)_n$-phenyl" includes benzyl, 2-phenylethyl, and 3-phenylpropyl.

The alkyl, alkenyl, and phenyl groups can be substituted with up to three groups such as hydroxy, alkoxy, halo, amino, alkylamino, and dialkylamino. Examples include chloromethyl, methoxymethyl, 2-hydroxyethyl, 4-amino-2-butenyl, 3,4-dibromobenzyl, 3,4,5-trimethoxybenzyl, and the like.

The term "movement disorders" as used herein means neurological diseases that are manifested in uncontrolled body motions. Typical movement disorders include ataxia, tardive dyskinesia, Tourette's syndrome, Wilson disease, dystonia, writer's cramp, essential tremor, Huntington's disease, multiple system atrophy, myoclonus, Parkinson's disease, progressive supranuclear palsy, restless leg syndrome, Rett syndrome, spasticity due to stroke, cerebral palsy, multiple sclerosis, spinal cord or brain injury.

"Patient" means a mammal, and includes humans, dogs, cats, horses, cattle, and sheep.

"Effective amount" means the quantity of a compound of Formula I required to treat the movement disorder being suffered by the patient.

"Halo" means fluoro, chloro, bromo, or iodo.

The compounds of Formula I can exist as pharmaceutically-acceptable salts. The term "pharmaceutically acceptable salt" as used herein refers to the addition salts of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic, and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, and the like. Invention salts include cations based on the alkali and alkaline earth metals such as sodium, lithium, potassium, calcium, magnesium, and the like, as well as, nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Berge S. M. et al., Pharmaceutical Salts, *J. Pharm. Sci.*, 1977;66:1–19 which is incorporated herein by reference.)

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention. Some of the compounds may have chiral centers, and this invention includes all racemates and individual enantiomers, as well as all geometric isomers.

The compounds of Formula I are readily prepared by methods utilizing standard organic chemical reactions. The starting materials are available from commercial sources or can be prepared from common reactants using standard methodologies. A typical synthesis of invention compounds of Formula I is illustrated in Scheme 1, in which a 5-hydroxy-4-dimethylamino indole is coupled with a dihydroisoquinoline. These reactants undergo a Diels-Alder condensation to provide desired benzoxazines of Formula I.

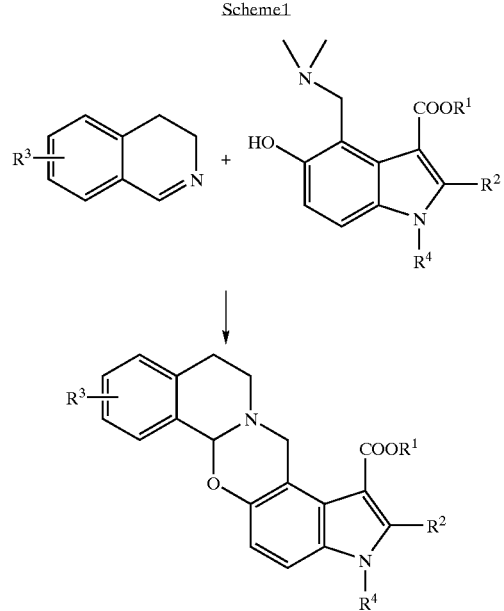

The indole Mannich base and dihydroisoquinoline generally are mixed in a neutral solvent such as dioxane, and the solution generally is stirred for about 2 to 6 hours at elevated temperatures of about 80° C. to about 150° C. The product benzoxazine is readily isolated by removal of the reaction solvents, and it can be further purified if desired by crystallization, chromatography, salt formation, and the like.

The reactants required to prepare benzoxazines according to Scheme 1 are either commercially available or are readily prepared by standard methods. The isoquinolines are prepared according to Schemes 2 and 3, and the indole Mannich base is prepared according to Scheme 4.

Scheme 2 illustrates the synthesis of 6-methoxy-3,4-dihydro-isoquinoline (III). The condensation reaction of N-[2-(3-methoxy-phenyl)-ethyl]-formamide (I) with formic acid is followed by Bischler-Napieralski ring closure.

Scheme 3 depicts the synthesis of 6-methylsulfanyl-3,4-dihydro-isoquinoline (XII). 3-Amino-benzoic acid (IV) is diazotized, reacted with sodium ethyl xanthate, followed by saponification, and is alkylated with dimethyl sulfate to give 3-methylsulfanyl-benzoic acid (V). This acid is reduced with Red-Al® (sodium bis (2-methoxyethoxy) aluminum hydride in toluene, Aldrich, Milwaukee, Wis., USA) to yield the alcohol (VI) which is converted to a benzyl chloride (VII) using thionyl chloride. The benzyl nitrile compound (VIII) is synthesized by treating (VII) with potassium cyanide in the presence of 18-crown-6. Standard reduction conditions (e.g., Raney nickel) gives phenethyl carbamate (IX), and deprotection yields the phenethylamine (X). (XI) is obtained by treating (X) with ethyl formate, followed by ring closure using phosphorus oxychloride to give the desired dihydroisoquinoline (XII).

Scheme 4 illustrates the condensation conditions of a ketoester (XIII) and a substituted amine ($R^3NH_2$) to yield the ene amino ester (XIV), which is then used for the Nenitzescu reaction to give a substituted 5-hydroxy-indole (XV). Standard Mannich reaction conditions affords the Mannich base (XVI).

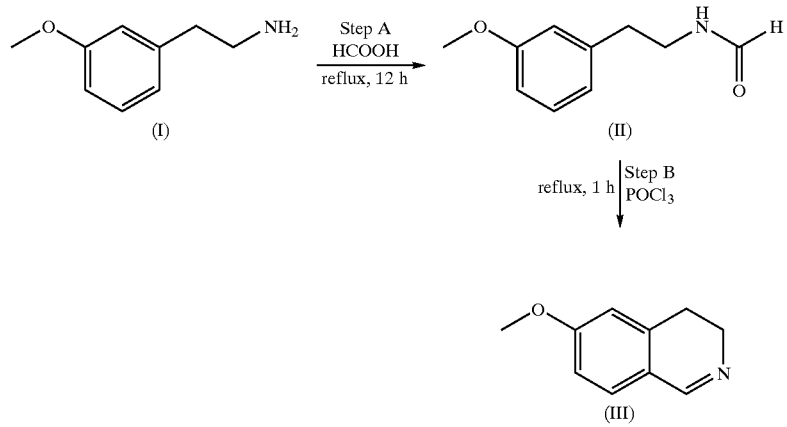

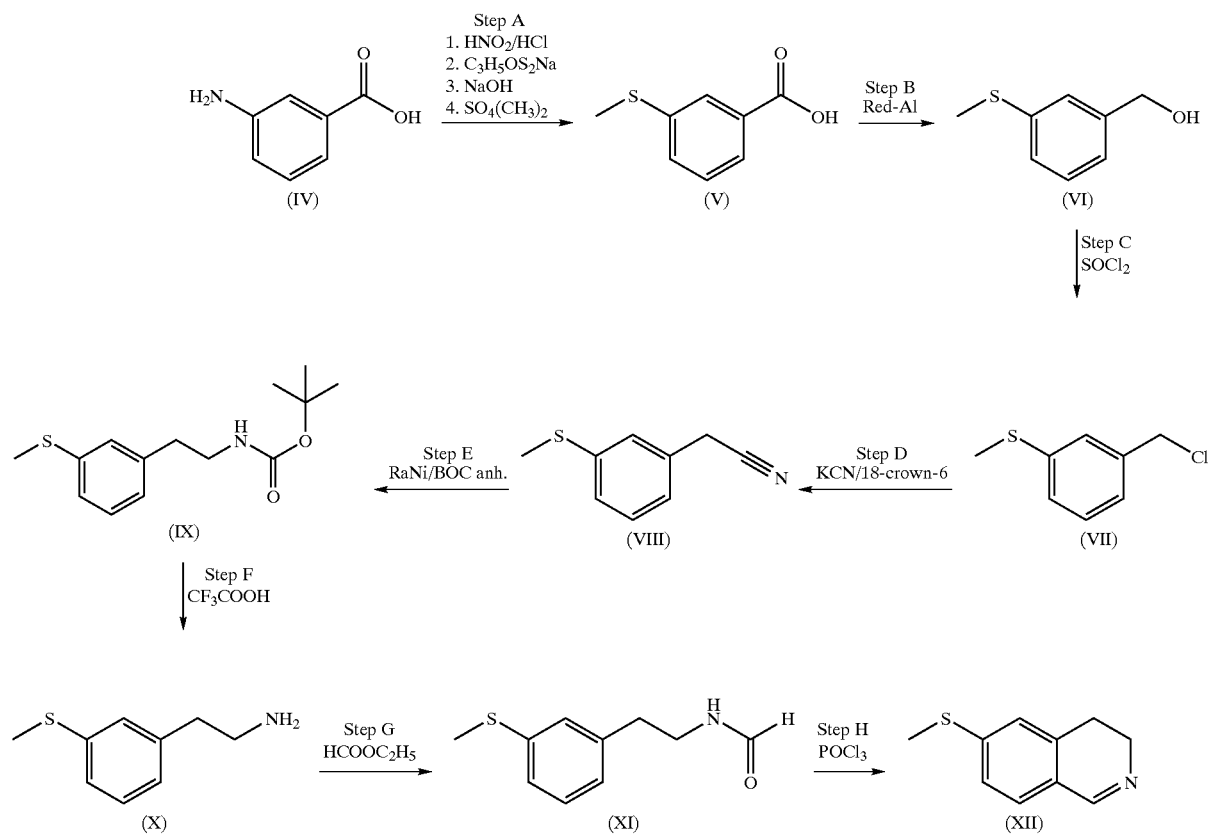

Scheme 4
Formation of Indoles

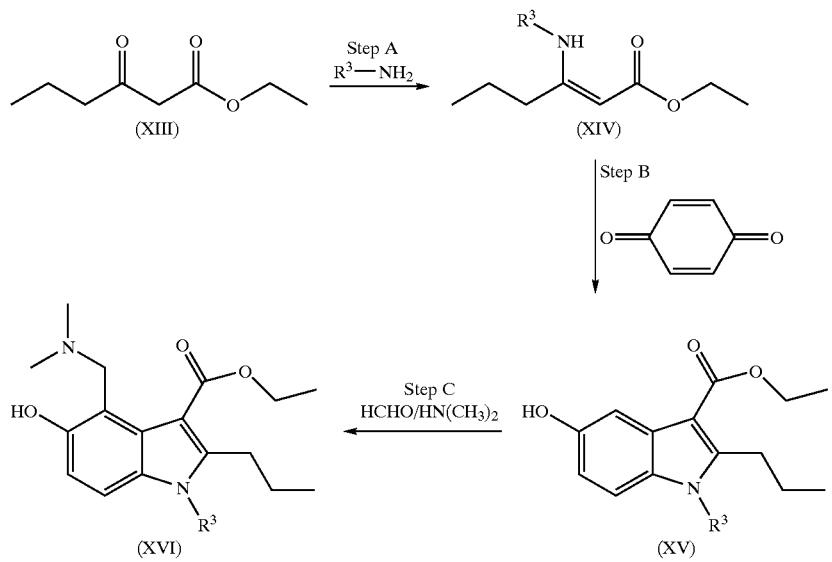

It may be desirable to use protecting groups for exposed functional groups during synthesis of intermediates and invention compounds. The use of protecting groups on hydroxy, amino, and carboxylic acid functional groups is common in organic synthetic methodologies so as to avoid unwanted side reactions during a particular chemical conversion. The use of protecting groups is fully described by Greene and Wuts in *Protecting Groups in Organic Synthesis*, (John Wiley & Sons Press, $2^{nd}$ ed), which is incorporated herein by reference. Typical hydroxy protecting groups include ester forming groups such as formyl and acetyl. Amines generally are protected with acyl groups such as acetyl, benzoyl, or tert.-butoxycarbonyl (BOC), and with groups such as trimethylsilyl or benzyl. Carboxylic acids generally are protected by esterification with groups such as 2,2,2-trichloroethyl and benzyl. All such protecting groups are readily removed by standard methods.

The following detailed examples illustrate the synthesis of specific invention compounds of Formula I. The examples are provided by way of illustration only, and are not to be construed as limiting the invention in any respect. The compounds will be named as substituted diazabenzo[a]cyclopent[h]anthracenes by reference to the numbering shown in the following formula:

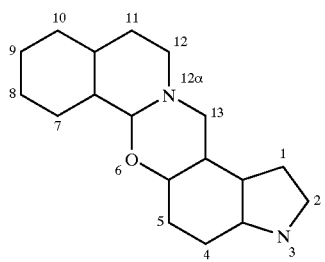

EXAMPLE 1

9-Methoxy-2-propyl-11,12-dihydro-3H,6αH,13H-6-oxa-3,12α-diaza-benzo[a]cyclopent[h]anthracene-1-carboxylic acid ethyl ester Preparation of N-[2-(3-methoxy-phenyl)-ethyl]-formamide (Step A, Scheme 2)

A solution of 2-(3-methoxy-phenyl)-ethylamine (50.0 g, 0.33 mol) in formic acid (60 mL) was refluxed overnight. Water (250 mL) was added and the emulsion extracted with ethyl acetate (2×150 mL). The organic layer was separated, dried ($Na_2SO_4$) and concentrated to give N-[2-(3-methoxy-phenyl)-ethyl]-formamide (43.1 g, 73%). MS: 180.1 ($M^+1^+$).

Preparation of 6-Methoxy-3,4-dihydro-isoquinoline (Step B, Scheme 2)

Phosphorus oxychloride (80 mL, 0.85 mol) was added dropwise to N-[2-(3-methoxy-phenyl)-ethyl]-formamide (41.1 g, 0.24 mol) and refluxed for 1 hour. The reaction mixture was cooled to room temperature, and hexane (3×500 mL) was added and decanted off three times. To the dark oily solution was added slowly water (200 mL) while stirring. The mixture was basified with NaOH to pH>13, extracted with ethyl acetate, dried ($Na_2SO_4$) and concentrated to afford the desired product (26.1 g, 67%). MS: 162.1 ($M^+1^+$).

Preparation of 5-Hydroxy-2-propyl-1H-indole-3-carboxylic acid ethyl ester (Step A, B, Scheme 4).

Through a solution of ethyl butyrylacetate (23 g, 0.145 mol) in methanol (200 mL) was bubbled ammonia at 5° C. for 15 minutes and then stirred at room temperature for 24 hours. The reaction mixture was concentrated to about 20 mL. Acetic acid (150 mL) and 1,4-benzoquinone (15.7 g, 0.145 mol) was added to the reaction mixture and it was stirred for 3 hours at room temperature. The suspension that formed was filtered, washed with $CH_2Cl_2$ (2×50 mL), and the solid residue was dried in a vacuum oven at 50° C. for 24 hours to give the desired product (2.2 g, 6%). MS: 248.1 ($M^+1^+$).

Preparation of 4-(Dimethyl-aminomethyl)-5-hydroxy-2-propyl-1H-indole-3-carboxylic acid ethyl ester (Step C, Scheme 4)

To solution of 5-hydroxy-2-propyl-1H-indole-3-carboxylic acid ethyl ester (2.2 g, 8.9 mmol) in ethanol (20 mL) was added formaldehyde 37% (0.85 mL, 10.7 mmol) and dimethylamine 40% (2.2 mL, 19.6 mmol). The reaction mixture was stored at 50° C. overnight, diluted with water (200 mL), and extracted with $CH_2Cl_2$ (3×50 mL). While adding HCl 7% solid material precipitated. The water layer was filtered and the solid residue basified with $K_2CO_3$ 10%, extracted with $CH_2Cl_2$ (3×50 mL), dried ($Na_2SO_4$) and concentrated to give the desired product (1.2 g, 44%). MS: 305.1 ($M^+1^+$).

Preparation of 9-Methoxy-2-propyl-11,12-dihydro-3H,6αH,13H-6-oxa-3,12α-diaza-benzo[a]cyclopent[h]anthracene-1-carboxylic acid ethyl ester (Scheme 1).

4-(Dimethyl-aminomethyl)-5-hydroxy-2-propyl-1H-indole-3-carboxylic acid ethyl ester (1.4 g, 4.6 mmol) and 6-methoxy-3,4-dihydro-isoquinoline (0.74 g, 4.6 mmol) were refluxed in Dioxane (20 mL) for 4 hours under a stream of nitrogen. The solution was concentrated and chromatographed with $CH_2Cl_2$/methanol to give the desired product (0.05 g, 5%). mp 191–193° C.

MS: 421.2 ($M^+1^+$) Analysis for $C_{25}H_{28}N_2O_4 \cdot 0.11H_2O$: Calcd: C, 71.07; H, 6.73; N, 6.63. Found: C, 70.69; H, 6.73; N, 6.50.

EXAMPLE 2

3-Methyl-9-methylsulfanyl-2-propyl-11,12-dihydro-3H,6aH,13H-6-oxa-3,12a-diaza-benzo[a]cyclopent[h]anthracene-1-carboxylic acid ethyl ester Preparation of 3-Methylsulfanyl-benzoic acid (Step A, Scheme 3)

The aminobenzoic acid (54.8 g, 0.4 mol) was diazotized in the usual manner with sodium nitrite (27.6 g, 0.4 mol) and hydrochloric acid (40 mL) and the resulting diazonium salt solution poured into a hot (70° C.), freshly prepared solution of potassium ethyl xanthate (64.2 g, 0.4 mol) containing sodium carbonate (55.2 g, 0.4 mol) to neutralize acid in the diazonium salt solution. After the reaction was over, as indicated by the cessation of the evolution of gases, the mixture was cooled. It was then treated with potassium hydroxide (24.7 g, 0.44 mol) and dimethyl sulfate (50.4 g, 0.4 mol). The mixture was refluxed for 5 hours. On acidification with hydrochloric acid, the desired product was obtained (38.2 g, 57%). MS: 167.8 ($M^+1^+$).

Preparation of (3-Methylsulfanyl-phenyl)-methanol (Step B, Scheme 3)

To a suspension of 3-methylsulfanyl-benzoic acid (38 g, 0.226 mol) in Toluene (500 mL) was added 200 mL of Red-Al® dropwise at 50° C. over 30 minutes. After stirring at room temperature for 3 hours, NaOH 10% (250 mL) was added while cooling with an ice-bath and then stirred overnight. The organic layer was separated and the water layer extracted twice with toluene (2×100 mL). The combined organic layers were dried ($K_2CO_3$), concentrated and distilled under reduced pressure to give the desired product (23.8 g, 68%). MS: 152,7 ($M^+1^{31}$).

Preparation of 1-Chloromethyl-3-methylsulfanyl-benzene (Step C, Scheme 3)

To a solution of (3-methylsulfanyl-phenyl)-methanol (23.8 g, 0.156 mol) in benzene (250 mL) was added thionyl chloride (26.9 g, 0.234 mol) under cooling with an ice-bath. The ice-bath was removed and the reaction mixture stirred for 48 hours at room temperature. The solution was concentrated and used without further work-up (26.9 g).

Preparation of (3-Methylsulfanyl-phenyl)-acetonitrile (Step D, Scheme 3)

To a solution of 1-chloromethyl-3-methylsulfanyl-benzene (26.9 g, 0.156 mol) and 18-crown-6 (2 g, 7.8 mmol) in dry acetonitrile (100 mL) was added potassium cyanide and stirred at room temperature for 48 hours. A precipitate was formed while adding dichloromethane (400 mL). The suspension was filtered, washed with water (2×150 mL), dried ($Na_2SO_4$) concentrated and distilled under reduced pressure to give a colorless oil (22.9 g, 91%). MS: 161.9 ($M^+1^-$).

Preparation of (3-Methylsulfanyl-phenyl)-ethyl] carbamic acid tert-butyl ester (Step E, Scheme 3)

To a solution of (3-methylsulfanyl-phenyl)-acetonitrile (22.9 g, 0.14 mol) and BOC anhydride. (47 g, 0.25 mol) in methanol (200 mL) was added Raney nickel (18 g). The mixture was shaken at room temperature for 48 hours. The mixture was filtered and concentrated. Chromatography with hexane/ethyl acetate gave the desired product (12 g, 33%). MS: 268.0 ($M^+1^+$).

Preparation of 2-(3-Methylsulfanyl-phenyl)-ethylamine (Step F, Scheme 3)

To a solution of (3-methylsulfanyl-phenyl)-ethyl] carbamic acid tert-butyl ester (12 g, 45 mmol) in $CH_2Cl_2$ (60 mL) was added trifluoroacetic acid (40 mL) and stirred for 10 minutes at room temperature. After the reaction was over, as indicated by the cessation of the evolution of gases, sodium hydroxide was added portionwise to pH>13. The emulsion was extracted with $CH_2Cl_2$ (3×100 mL), dried ($MgSO_4$), and concentrated to give an orange oil (7.4 g, 99%). MS: 167.9 ($M^+1^+$).

Preparation of N-[2-(3-Methylsulfanyl-phenyl)-ethyl]-formamide (Step G, Scheme 3)

A procedure identical to that described for the preparation of N-[2-(3-methoxy-phenyl)-ethyl]-formamide in Example 1 was followed using 2-(3-methylsulfanyl-phenyl)-ethylamine (7.4 g, 44 mmol) and formic acid ethyl ester (3.6 g, 48 mmol) to give the desired product (6.7 g, 78%). MS: 168.9 ($M^+1^+$).

Preparation of 6-Methylsulfanyl-3,4-dihydro-isoquinoline (Step H, Scheme 3)

A procedure identical to that described for the preparation of N-[2-(3-methoxy-phenyl)-ethyl]-formamide in Example 1 was followed using N-[2-(3-methylsulfanyl-phenyl)-ethyl]-formamide (6.7 g, 34 mmol) to give the desired product (0.8 g, 13%). MS: 178.1 ($M^+1^+$).

Preparation of 5-Hydroxy-1-methyl-2-propyl-1H-indole-3-carboxylic acid ethyl ester (Step A, B, Scheme 4)

A procedure identical to that described for the preparation of 5-hydroxy-2-propyl-1H-indole-3-carboxylic acid ester in Example 1 was followed using methylamine to give the desired product (6.1 g, 39%). MS: 262 ($M^+1^+$).

Preparation of 3-Methyl-9-methylsulfanyl-2-propyl-11,12-dihydro-3H,6aH,13H-6-oxa-3,12a-diaza-benzo[a]cyclopent[h]anthracene-1-carboxylic acid ethyl ester (Scheme 1)

A procedure identical to that described for the preparation of 9-methoxy-2-propyl-11,12-dihydro-3H,6αH,13H-6-oxa- 3,12α-diaza-benzo[a]cyclopent[h]-anthracene-1-carboxylic acid ethyl ester in Example 1 was followed to react 4-(dimethylaminomethyl)-5-hydroxy-2-propyl-1H-indole-3-carboxylic acid ethyl ester with 6-methylsulfanyl-3,4-dihydro-isoquinoline (0.8 g, 4.5 mmol) to give the desired product (0.035 g, 2%). mp 139–143° C. MS: 451.1 ($M^+1^+$).

Analysis for $C_{26}H_{30}N_2O_3S$ 0.27$H_2O$: Calcd: C, 68.56; H, 6.76; N, 6.15. Found: C, 68.19; H, 6.67; N, 6.02.

EXAMPLE 3
9-Methoxy-3-methyl-2-propyl-11,12-dihydro-3H,6aH,13H-6-oxa-3,12a-diaza-benzo[a]cyclopent[h]anthracene-1-carboxylic acid ethyl ester Preparation of 9-Methoxy-3-methyl-2-propyl-11,12-dihydro-3H,6aH,13H-6-oxa-3,12a-diaza-benzo[a]cyclopent[h]anthracene-1-carboxylic acid ethyl ester (Scheme 1)

By following the general procedure of Example 2 for the preparation of 9-methoxy-2-propyl-11,12-dihydro-3H,6αH, 13H-6-oxa-3,12α-diaza-benzo[a]cyclopent[h]anthracene-1-carboxylic acid ethyl ester, 4-(dimethylamino-methyl)-5-hydroxy-1-methyl-2-propyl-1H-indole-3-carboxylic acid ethyl ester (2.1 g, 6.6 mmol) was reacted with 6-methoxy-3,4-dihydro-isoquinoline (1.005 g, 6.6 mmol) to give the desired product (0.22 g, 8%). MP 150–151° C. MS: 435.2 ($M^+1^+$).

Analysis for $C_{26}H_{30}N_2O_4$: Calcd: C, 71.87; H, 6.96; N, 6.45. Found: C, 71.49; H, 6.89; N, 6.29.

EXAMPLES 4–8

The following invention compounds were prepared by following the general procedures described above in Examples 1–3.

9-Methylsulfanyl-2-propyl-11,12-dihydro-3H,6aH,13H-6-oxa-3,12a-diaza-benzo[a]cyclopent[h]anthracene-1-carboxylic acid ethyl ester, mp 185–186° C.;

2-Butyl-9-methoxy-11,12-dihydro-3H,6aH,13H-6-oxa-3,12a-diaza-benzo[a]cyclopent[h]anthracene-1-carboxylic acid ethyl ester, mp 180–182° C.;

2-Butyl-9-methylsulfanyl-11,12-dihydro-3H,6aH,13H-6-oxa-3,12a-diaza-benzo[a]cyclopent[h]anthracene-1-carboxylic acid ethyl ester, mp 159–161° C.;

9-Methoxy-2-pentyl-11,12-dihydro-3H,6aH,13H-6-oxa-3,12a-diaza-benzo[a]cyclopent[h]anthracene-1-carboxylic acid ethyl ester, mp 170–172° C.; and 2-Hexyl-9-methoxy-11,12-dihydro-3H,6aH,13H-6-oxa-3,12a-diaza-benzo[a]cyclopent[h]anthracene-1-carboxylic acid ethyl ester, mp 157–160° C.

The compounds of Formula I have shown potent binding affinity for muscarinic receptors and are thus useful as muscarinic antagonists. The compounds are surprisingly selective as muscarinic $M_4$ receptor antagonists. The compounds were evaluated in standard assays used to measure muscarinic receptor binding, and they were compared with other benzoxazines described in *Bioorganic & Medicinal Chemistry Letters* 8, 1998:1991–1996, which is incorporated herein by reference. Specifically, the compounds were evaluated for their binding affinity toward five human muscarinic receptor subtypes ($M_1$–$M_5$) by the method of Dorje et al., *J. Pharm. Exp. Ther.* 1991;256:727–733, which is incorporated herein by reference. The binding was determined by measuring the displacement of [$^3$H]-NMS (N-methylscopolamine) binding using membranes from transfected Chinese hamster ovary (CHO) cells. All compounds were tested two to four times with duplicate tubes (SEM is ≦10% in all cases). Table 1 shows the binding activities ($IC_{50}$ nM) of several prior art compounds compared to invention compounds.

TABLE 1

Muscarinic Binding Activity

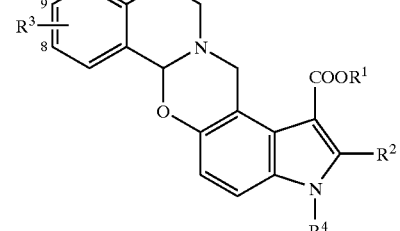

| Prior Art Compounds | | | | | | | | |
|---|---|---|---|---|---|---|---|---|
| $R^1$ | $R^2$ | $R^3$ | $R^4$ | $M_1$ | $M_2$ | $M_3$ | $M_4$ | $M_5$ |
| Et | Me | 9-OMe | H | 3000 | 1000 | 500 | 30 | 6000 |
| Et | Me | 9-OMe | Me | 500 | 400 | 400 | 50 | 1000 |
| Et | Me | 9-OMe | Et | 2000 | 400 | 500 | 50 | 3000 |
| Et | Et | 9-OMe | H | 2000 | 2000 | 200 | 20 | 6000 |
| Et | Et | 9-OMe | Et | 5000 | 1000 | 50 | 20 | 5000 |

| Invention Compounds | | | | | | | | | |
|---|---|---|---|---|---|---|---|---|---|
| Example No. | $R^1$ | $R^2$ | $R^3$ | $R^4$ | $M_1$ | $M_2$ | $M_3$ | $M_4$ | $M_5$ |
| 1 | Et | nPr | 9-OMe | H | 4660 | 2000 | 130 | 9 | 3660 |
| 2 | Et | nPr | 9-SMe | Me | 7500 | 7000 | 370 | 7 | 3000 |
| 3 | Et | nPr | 9-OMe | Me | 3000 | 950 | 130 | 7 | 6000 |
| 4 | Et | nPr | 9-SMe | H | 1400 | 2000 | 200 | 6 | 3500 |
| 5 | Et | nBu | 9-OMe | H | 800 | 550 | 190 | 6 | 13000 |
| 6 | Et | nBu | 9-SMe | H | 2000 | 4000 | 5000 | 10 | 2000 |
| 7 | Et | n-Pentyl | 9-OMe | H | 50000 | 600 | 200 | 10 | 10000 |
| 8 | Et | n-Hexyl | 9-OMe | H | 2000 | 800 | 400 | 30 | 3000 |

The data in Table 1 establishes that the invention compounds of Formula I are surprisingly potent and selective for binding to the $M_4$ receptor. "$M_4$ selective" as used herein means that a compound binds to the $M_4$ muscarinic receptor subtype by at least about 20-fold more than to any of the other receptor subtypes. For example, the invention compound of Example 2 binds to the $M_4$ receptor about 52-fold more than to $M_3$, and about 1000-fold more than to $M_1$, $M_2$, and $M_5$. The compounds of Examples 4 and 5 bind to $M_4$ by about 30-fold more than to the $M_3$, and by as much as about 800-fold more than some of the other subtypes. The prior art compounds are not $M_4$ selective because they show binding affinity of only about 2- to about 15-fold more at $M_4$ than to any of the other receptors. Because of the potency and $M_4$ selectivity of the invention compounds, they are particularly useful for treatment of movement disorders such as Parkinson's disease.

For use in treating movement disorders, the invention compound is typically part of a pharmaceutical composition and is administered to a patient by methods well-known to those skilled in the art. The invention compound will be present in an amount of about 5% to about 95% by weight of the composition.

In the methods of the present invention, a compound can be administered either orally, rectally, parenterally (intravenous, intramuscularly, or subcutaneously), intracisternally, intravaginally, intraperitoneally, intravesically, locally (powders, ointments, patches, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft- and hard-filled gelatin capsules using such excipients as lactose or milk sugar, as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, and sesame oil, glycerol, tetrahydrofurfuryl alcohol, polyethyleneglycols, and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable nonirritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers or propellants as may be required. Ophthalmic formulations, eye ointments, powders, and solutions are also contemplated as being within the scope of this invention. Controlled release compositions in the form of skin patches and the like also are provided.

Typical doses of invention compounds will be from about 0.1 to about 1000 mg/kg, and generally from about 5 to about 250 mg/kg. Such doses can be administered from one to about four times each day, or as often as an attending physician may direct.

The following examples illustrate typical compositions provided by this invention.

EXAMPLE 9

Tablet Formulation

| Ingredient | Amount |
| --- | --- |
| Compound of Example 1 | 50 mg |
| Lactose | 80 mg |
| Cornstarch (for mix) | 10 mg |
| Cornstarch (for paste) | 8 mg |
| Magnesium Stearate (1%) | 2 mg |
| | 150 mg |

The compound of Example 1 is mixed with the lactose and cornstarch (for mix) and blended to uniformity to a powder. The cornstarch (for paste) is suspended in 6 mL ofwater and heated with stirring to form a paste. The paste is added to the mixed powder, and the mixture is granulated. The wet granules are passed through a No. 8 hard screen and dried at 50° C. The mixture is lubricated with 1% magnesium sterate and compressed into a tablet. The tablets are administered to a patient at the rate of 1 to 4 each day for treatment of Parkinson's disease and other movement disorders.

EXAMPLE 10

Parenteral Solution

In a solution of 700 mL of propylene glycol and 200 mL of water for injection is added 20.0 g of the compound of Example 2. The mixture is stirred, and the pH is adjusted to 5.5 with hydrochloric acid. The volume is adjusted to 1000 mL with water for injection. The solution is sterilized, filled into 5.0 mL ampoules, each containing 2.0 mL (40 mg of Example 2), and sealed under nitrogen. The solution is administered by injection to a patient suffering from Parkinson's disease or other movement disorder and in need of treatment.

EXAMPLE 11

Patch Formulation

Ten milligrams of 9-methoxy-3-methyl-2-propyl-11,12-dihydro-3H,6aH,13H-6-oxa-3,12a-diaza-benzo[a]cyclopent[h]anthracene-1-carboxylic acid ethyl ester is mixed with 1 mL of propylene glycol and 2 mg of acrylic-based polymer adhesive containing a resinous cross-linking agent. The mixture is applied to an impermeable backing (30 cm$^2$) and applied to the upper back of a patient for sustained release treatment of Parkinson's disease or other movement disorder.

A further embodiment of the invention is a method for treating movement disorders comprising administering to a patient suffering from a movement disorder and in need of treatment an effective amount of a compound of Formula I. An "effective amount" is that quantity of invention compound that produces a positive clinical reaction in a patient suffering from a movement disorder. An effective amount is generally about 0.1 to about 1000 mg/kg. A preferred dosage will be from about 1.0 to about 500 mg/kg, and more preferably about 5 to about 250 mg/kg. In a preferred embodiment, the invention provides a method for treating Parkinson's disease comprising administering to a patient an effective amount of a compound of Formula I.

The invention and the manner and process of making and using it, are now described in such full, clear, concise, and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

We claim:

1. A compound of Formula I

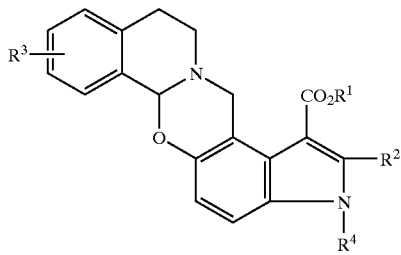

or a pharmaceutically acceptable salt thereof, wherein:

$R^1$ is $C_1$–$C_6$ alkyl, $C_2$–$C_6$ alkenyl, or $(CH_2)_n$phenyl;

$R^2$ is $C_3$–$C_6$ alkyl;

$R^3$ is hydrogen, halo, hydroxy, O—$C_1$–$C_6$ alkyl, or S—$C_1$–$C_6$ alkyl;

$R^4$ is hydrogen, $C_1$–$C_6$ alkyl, or $(CH_2)_n$phenyl; and n is an integer from 0 to 3.

2. A compound of claim 1 wherein $R^1$ is ethyl.

3. A compound of claim 2 wherein $R^2$ is n-propyl, n-butyl, n-pentyl, or n-hexyl.

4. A compound of claim 3 wherein $R^4$ is hydrogen or methyl.

5. 3-methyl-9-methylsulfanyl-2-propyl-11,12-dihydro-3H,6aH,13H-6-oxa-3,12a-diaza-benzo[a]cyclopent[h]anthracene-1-carboxylic acid ethyl ester.

6. 9-methoxy-2-propyl-11,12-dihydro-3H,6aH,13H-6-oxa-3,12a-diaza-benzo[a]cyclopent[h]anthracene-1-carboxylic acid ethyl ester.

7. 9-methoxy-3-methyl-2-propyl-11,12-dihydro-3H,6aH,13H-6-oxa-3,12a-diaza-benzo[a]cyclopent[h]anthracene-1-carboxylic acid ethyl ester.

8. A compound selected from the group consisting of

9-Methylsulfanyl-2-propyl-11,12-dihydro-3H,6aH,13H-6-oxa-3,12-dihydro-3H,6aH,13H-6-oxa-3,12a-diaza-benzo[a]cyclopent[h]anthracene-1-carboxylic acid ethyl ester;

2-Butyl-9-methoxy-11,12-dihydro-3H,6aH,13H-6-oxa-3,12a-diaza-benzo[a]cyclopent[h]anthracene-1-carboxylic acid ethyl ester;

2-Butyl-9-methylsulfanyl-11,12-dihydro-3H,6aH,13H-6-oxa-3,12a-diaza-benzo[a]cyclopent[h]anthracene-1-carboxylic acid ethyl ester;

9-Methoxy-2-pentyl-11,12-dihydro-3H,6aH,13H-6-oxa-3,12a-diaza-benzo[a]cyclopent[h]anthracene-1-carboxylic acid ethyl ester; and 2-Hexyl-9-methoxy-11,12-dihydro-3H,6aH,13H-6-oxa-3,12a-diazo-benzo[a]cyclopent[h]anthracene-1-carboxylic acid ethyl ester.

9. A pharmaceutical composition comprising a compound of claim 1 together with a pharmaceutically acceptable diluent, excipient, or carrier therefor.

10. A method for treating movement disorders comprising administering to a patient suffering from a movement disorder and in need of treatment an effective amount of a compound of claim 1.

11. A method according to claim 10 wherein the movement disorder is Parkinson's disease.

* * * * *